(12) United States Patent
Cohen et al.

(10) Patent No.: US 6,172,091 B1
(45) Date of Patent: Jan. 9, 2001

(54) 1,2-DISUBSTITUTED CYCLOPROPANES

(75) Inventors: Judith Hope Cohen, North Wales, PA (US); Donald Ward Combs, Piscataway; Philip James Rybczynski, Branchburg, both of NJ (US)

(73) Assignee: Ortho-McNeil Pharmaceutical, Inc., Raritan, NJ (US)

( * ) Notice: Under 35 U.S.C. 154(b), the term of this patent shall be extended for 0 days.

(21) Appl. No.: 09/417,319

(22) Filed: Oct. 13, 1999

Related U.S. Application Data

(60) Provisional application No. 60/104,132, filed on Oct. 14, 1998.

(51) Int. Cl.$^7$ .................. C07D 213/02; A61K 31/44; A61K 31/165; C07C 233/18
(52) U.S. Cl. .................. 514/357; 514/427; 514/438; 514/649; 546/329; 548/566; 549/74; 564/161; 564/192; 564/336
(58) Field of Search .................. 564/161, 192, 564/336; 514/649, 357, 427, 438; 546/329; 548/566; 549/74

(56) References Cited

U.S. PATENT DOCUMENTS

| 5,034,419 | 7/1991 | Aubard et al. | 514/649 |
|---|---|---|---|
| 5,169,780 | 12/1992 | Stirling et al. | 435/280 |
| 5,753,709 | 5/1998 | Keavy et al. | 514/630 |

FOREIGN PATENT DOCUMENTS

| 0 326 934 B1 | 10/1991 | (EP) . |
|---|---|---|
| 0747346 A2 | 12/1996 | (EP) . |
| 0747346 A3 | 11/1997 | (EP) . |
| WO 93/04373 | 3/1994 | (WO) . |
| WO 94/18959 | 9/1994 | (WO) . |
| WO 95/21612 | 8/1995 | (WO) . |
| WO 96/02492 | 2/1996 | (WO) . |
| WO 96/05818 | 2/1996 | (WO) . |
| WO 96/12697 | 5/1996 | (WO) . |
| WO 96/40097 | 12/1996 | (WO) . |

OTHER PUBLICATIONS

Borne, R.F. et al.; Conformational Analogues of Antihypertensive Agents Related to Guanethidine; Journal of Med. Chem., 1977, vol. 20, No. 6 pp. 771–776.

Teotino, et al; Chemical and Biological Properties of Some Aminoethyl-2-phenylcyclopropane Derivatives. Pharmacological Comparison with Tranylcypromine; vol. 10, Nov. 1967; pp. 1091–1096.

Giannis, A. et al.; LiBH$_4$(NaBH$_4$) /Me$_3$SiCl, an Unusually Strong and Versatile Reducing Agent; Angew. Chem. Int.Ed. Engl. 28 (1989) No. 2;pp. 218–220.

*Primary Examiner*—Zinna Northington Davis

(57) ABSTRACT

Compounds of Formula I

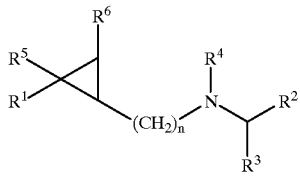

wherein the substituents are as described in the specification or pharmaceutically acceptable salts or stereochemically isomeric forms thereof, useful for treating diseases related to calcium imbalance and metabolism.

13 Claims, No Drawings

1,2-DISUBSTITUTED CYCLOPROPANES

CROSS REFERENCE TO RELATED APPLICATIONS

This application claims priority from U.S. provisional application Ser. No. 60/104,132, filed Oct. 14, 1998 the contents of which are hereby incorporated by reference.

FIELD OF THE INVENTION

This invention relates to novel cyclopropane derivatives, pharmaceutical compositions containing them and methods of using them. The compounds of the invention bind to the calcium-sensing receptor and thus, are useful in treating diseases related to calcium imbalance and metabolism.

BACKGROUND OF THE INVENTION

Known cyclopropane derivatives include secondary and tertiary cyclopropyl methylamines described in Teotino, U. M.; Della Bella, D.; Gandini, A.; Benelli, G., *J. Med. Chem.* 1967, Vol. 10, p. 1091 as monoamine oxidase inhibitors; and cyclopropyl-methylguanidines described in Borne, R. F.; Forrester, M. L.; Waters, I. W., *J. Med Chem*, Vol. 20, p. 771 (1977) as useful in treating hypertension. GB 1,086,191 discloses certain phenyl cyclopropane derivatives.

Extracellular calcium can exert effects on different cell functions as discussed in Nemeth et al., 11 Cell Calcium 319,1990. The role of extracellular calcium in parafollicular and parathyroid cells is discussed in Nemeth, et al., 11 Cell Calcium 323,1990.

PCT/US93/01642 (WO 94/18959); PCT/US95/13704 (WO 96/12697) and PCT/US92/07175 (WO 93/04373) disclose compounds which are described as modulators of inorganic ion receptor activity, such as mimicing or blocking the effect of extracellular calcium on a cell surface calcireceptor.

SUMMARY OF THE INVENTION

The present invention is directed to compounds of Formula I

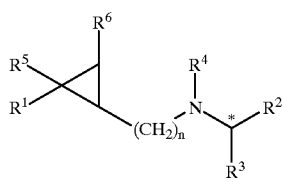

wherein
- $R^1$ is unsubstituted aryl; or aryl substituted with at least one substituent selected from the group consisting of $C_1-C_6$ alkyl, cycloalkyl, halogen, haloalkyl, nitro, and $C_1-C_6$ alkoxy;
- $R^2$ is phenyl substituted with at least one substituent selected from $C_1-C_6$ alkyl, cycloalkyl, haloalkyl, chloro, fluoro, iodo, $C_1-C_6$ alkoxy, alkylthio, arylthio, alkylsulfone, arylsulfone, hydroxy, hydroxy alkyl, —$COOR^7$ and $CON(R^8)_2$; unsubstituted heteroaryl or heteroaryl substituted with at least one substituent selected from $C_1-C_6$ alkyl, cycloalkyl, haloalkyl, chloro, fluoro and iodo;
- $R^3$ is hydrogen, $C_1-C_6$ alkyl or $C_1-C_6$ geminal dialkyl;
- $R^4$ is hydrogen, $CON(R^9)_2$, $SO_2N(R^{10})_2$, $COR^{11}$ or $COOR^{12}$;
- $R^5$, $R^6$, $R^7$, $R^8$, $R^9$, $R^{10}$, $R^{11}$, and $R^{12}$ are independently selected from hydrogen or alkyl; and
- n is 1;

or a pharmaceutically acceptable salt or stereochemically isomeric form thereof.

The compounds of formula I bind to the calcium-sensing receptor and thus are useful in treating diseases related to calcium imbalance and metabolism. Such diseases include hyperparathyroidism, osteoporosis, Paget's disease, hypercalcemia malignancy, hypertension and renal osteodystrophy.

The present invention also relates to pharmaceutical compositions containing one or more of the compounds of formula I and methods for the treatment of disorders related to calcium imbalance, such as, hyperparathyroidism, osteoporosis, and the like.

In another aspect, the claimed invention relates to intermediates of formula

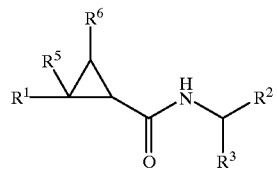

wherein $R^1$, $R^2$ and $R^3$ are as described above, and one of $R^5$ and $R^6$ is alkyl and the other is hydrogen or both $R^5$ and $R^6$ are alkyl.

DETAILED DESCRIPTION OF THE INVENTION

As used herein the term alkyl, alone or in combination, refers to straight, cyclic and branched-chain alkyl groups. For example, alkyl radicals include methyl, ethyl, propyl, isopropyl, butyl, isobutyl, sec-butyl, t-butyl and the like, preferably $C_1-C_6$ alkyl. Alkoxy radicals are oxygen ethers formed from the previously described straight or branched chain alkyl groups, $C_1-C_6$ alkoxy is preferred. The term "aryl" as used herein, alone or in combination with other terms, indicates aromatic hydrocarbon groups such as phenyl or naphthyl, more particularly preferred is phenyl and heteroaromatic cyclic groups ("heteroaryls") such as furan, pyridine, thiophene and pyrrole, preferably the heteroaromatic cyclic group is a 5 or 6 membered ring wherein the hetero atom is at least one of N, S or O, more preferred is one hetero atom. With reference to substituents, the term independently means that when more than one of such substituent is possible, such substituents may be the same or different from each other. The term halogen defines fluoro, chloro, bromo and iodo.

When compounds of formula I contain a basic moiety, acid addition salts may be prepared. Examples of suitable acids to form such salts include hydrochloric, hydrobromic, hydroiodic, perchloric, sulfuric, nitric, phosphoric, acetic, propionic, glycolic, lactic, pyruvic, oxalic, malonic, succinic, maleic, fumaric, malic, tartaric, citric, benzoic, cinnamic, mandelic, methanesulfonic, p-toluenesulfonic, cyclo hexanesulfamic, salicylic, 2-phenoxybenzoic or 2-acetoxybenzoic, and the like. Such salts can be made by known methods of reacting the free base of compounds of formula I with the acid and isolating the salt.

Stereochemistry of the cyclopropane is cis or trans, preferably trans, and absolute stereochemistry at the stereogenic center identified in formula I by an asterisk is R or S, preferably R.

The term stereochemically isomeric forms as used herein defines the different isomeric forms which the compounds of formula I may possess. Unless otherwise mentioned or indicated, the chemical designation of compounds denotes the mixture of all possible stereochemically isomeric forms, said mixtures containing all diastereomers and/or enantiomers of the basic molecular structure. All stereochemically isomeric forms of the compounds of formula I both in pure form or in admixture with each other are intended to be embraced within the scope of the present invention can be obtained using conventional means.

The present invention is directed to compounds of Formula I

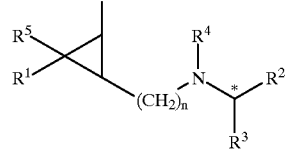

wherein
- $R^1$ is unsubstituted aryl; or aryl substituted with at least one substituent selected from the group consisting of $C_1$–$C_6$ alkyl, cycloalkyl, halogen, haloalkyl, nitro, and alkoxy;
- $R^2$ is phenyl substituted with at least one substituent selected from $C_1$–$C_6$ alkyl, cycloalkyl, haloalkyl, chloro, fluoro, iodo, $C_1$–$C_6$ alkoxy, alkylthio, alkylsulfone, arylsulfone, hydroxy, hydroxyalkyl, —$COOR^7$ and $CON(R^8)_2$;
- $R^3$ is hydrogen, $C_1$–$C_6$ alkyl or $C_1$–$C_6$ geminal dialkyl;
- $R^4$ is hydrogen, $CON(R^9)_2$, $SO_2N(R^{10})_2$, $COR^{11}$ or $COOR^{12}$;
- $R^5$, $R^6$, $R^7$, $R^8$, $R^9$, $R^{10}$, $R^{11}$, and $R^{12}$ are independently selected from hydrogen or alkyl; and
- n is 1;

or a pharmaceutically acceptable salt or stereochemically isomeric form thereof.

Of particular interest are those compounds wherein $R^1$ is unsubstituted aryl or aryl substituted with halogen or $C_1$–$C_6$ alkyl; $R^2$ is unsubstituted pyridyl, pyridyl substituted with at least one of $C_1$–$C_6$ alkyl, cycloalkyl, haloalkyl, chloro, fluoro or iodo, or phenyl substituted with at least one substituent selected from $C_1$–$C_6$ alkyl, cycloalkyl, haloalkyl, chloro, fluoro, iodo, $C_1$–$C_6$ alkoxy, alkylthio, alkylsulfone, arylsulfone, hydroxy, hydroxyalkyl, —$COOR^7$ and $CON(R^8)_2$; stereochemistry at the cyclopropane is trans, preferably R,R absolute configuration; $R^3$ is alkyl, preferably methyl and $R^4$ is hydrogen, $CON(R^9)_2$, $COR^{11}$ or $COOR^{12}$, preferably hydrogen.

More preferred are compounds of formula I wherein $R^1$ is unsubstituted phenyl or thiophene or phenyl or thiophene substituted with halogen or $C_1$–$C_6$ alkyl; $R^3$ is phenyl substituted with $C_1$–$C_6$ alkyl, chloro, fluoro, iodo or $C_1$–$C_6$ alkoxy.

In particularly preferred compounds, $R^1$ is unsubstituted phenyl or thiophene and $R^2$ is phenyl substituted with $C_1$–$C_6$ alkoxy.

The absolute stereochemistry is most preferably RRR.

In a particularly preferred embodiment, the compound of formula I is N-((R,R)-2-phenylcyclopropanylmethyl)-1-(R)-(3-methoxyphenyl)ethylamine, represented by formula IA.

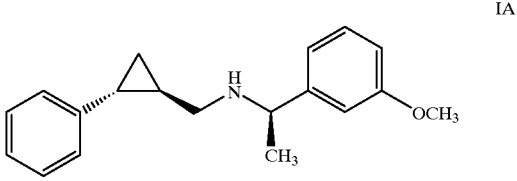

The compounds of formula I are prepared as outlined in Schemes 1–6.

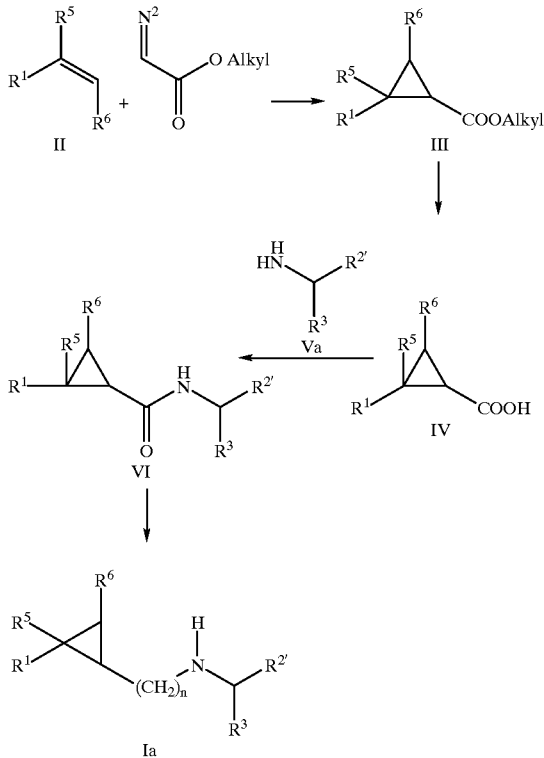

wherein $R^1$, $R^3$, $R^5$ and $R^6$ are as described above and $R^{2'}$ is as described above for $R^2$ except that $R^{2'}$ is not phenyl substituted with at least one substituent selected from alkylsulfone, arylsulfone, —$COOR^7$ and —$CON(R^8)_2$.

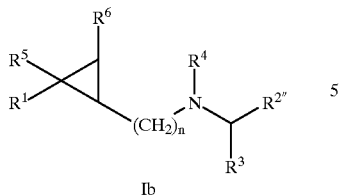

Ib wherein $R^1$, $R^3$, $R^4$, $R^5$ and $R^6$ are as described above and $R^{2''}$ is phenyl substituted with at least one substituent selected from alkylsulfone, arylsulfone, —COOR$^7$ and CON(R$^8$)$_2$.

As set forth in Scheme 1 above, the styrene of formula II, a known compound or compound prepared by known methods, is reacted with an alkyl diazoacetate, a known compound or compound prepared by known methods, at reflux in a high boiling inert solvent, such as xylene, to yield the corresponding compound of formula III which is then selectively saponified, for example, with a metal hydroxide, such as, potassium or sodium hydroxide to form the corresponding compound of formula IV. Optionally, the compound of formula III is separated into its cis and trans components by known methods (*Org. Syn. Coll. Vol. VI* 1988, 913). The compound of formula IV is converted to the corresponding compound of formula VI by reacting, preferably at room temperature with a compound of formula Va, in an aprotic polar solvent, such as acetonitrile and a coupling reagent such as dicyclohexylcarbodiimide. (*Aust. J. Chem.* 1984, 37, 1709). The compound of formula VI is reduced to the corresponding compound of formula Ia with a reducing agent, such as with BH$_3$ in tetrahydrofuran (THF) or with lithium or sodium borohydride followed by addition of chlorotrimethylsilane, at elevated temperatures in the range of 50° C. to reflux.

Alternatively, as set forth in Scheme Ib, a compound of formula IV can be reduced to the corresponding primary alcohol of formula VII with a reducing agent such as BH$_3$, preferably at room temperature. The compound of formula VII can be converted to the corresponding compound of formula Ib by a displacement reaction, such as, a Mitsunobu reaction, with a compound of formula Vb.

Scheme 2a

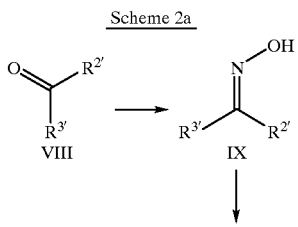

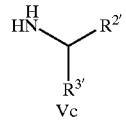

Vc wherein $R^{2'}$ is as described above for $R^2$ except that $R^{2'}$ is not phenyl substituted with at least one substituent selected from alkylsulfone, arylsulfone, —COOR$^7$ and —CON(R$^8$)$_2$; $R^{3'}$ is hydrogen or C$_1$–C$_6$ alkyl.

Intermediates of formula Vc are prepared as set forth in Scheme 2a. A compound of formula VIII, a known compound or compound prepared by known methods, is converted to the corresponding compound of formula IX by heating with hydroxylamine in a polar solvent such as ethanol, preferably at about 60 to 80° C. The compound of formula IX is reduced, preferably at room temperature, to the corresponding compound of formula Vc preferably by reacting with hydrogen gas and a catalyst, such as, palladium, in a polar solvent such as methanol.

Scheme 2b

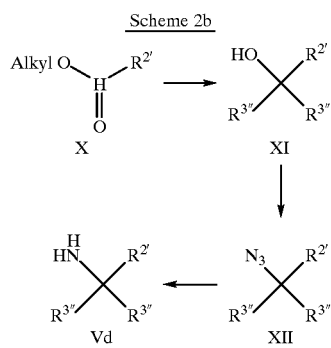

wherein $R^{2'}$ is as described above and $R^{3''}$ is C$_1$–C$_6$ alkyl.

Intermediates of formula Vd are prepared as set forth in Scheme 2b. A compound of formula X is reacted with a carbon nucleophile, such as, methyl magnesium bromide in a non polar aprotic solvent, such as, diethyl ether to form the corresponding compound of formula XI. The compound of formula XI is reacted with an azide delivering agent, such as, diphenylphosphoryl azide in a non polar solvent, such as, toluene to form the corresponding compound of formula XII. The compound of formula XII is reduced to the amine, preferably by reacting with a hydrogen gas and a catalyst, such as, palladium in a polar solvent such as ethanol to form the corresponding intermediate of formula Vd.

Scheme 3

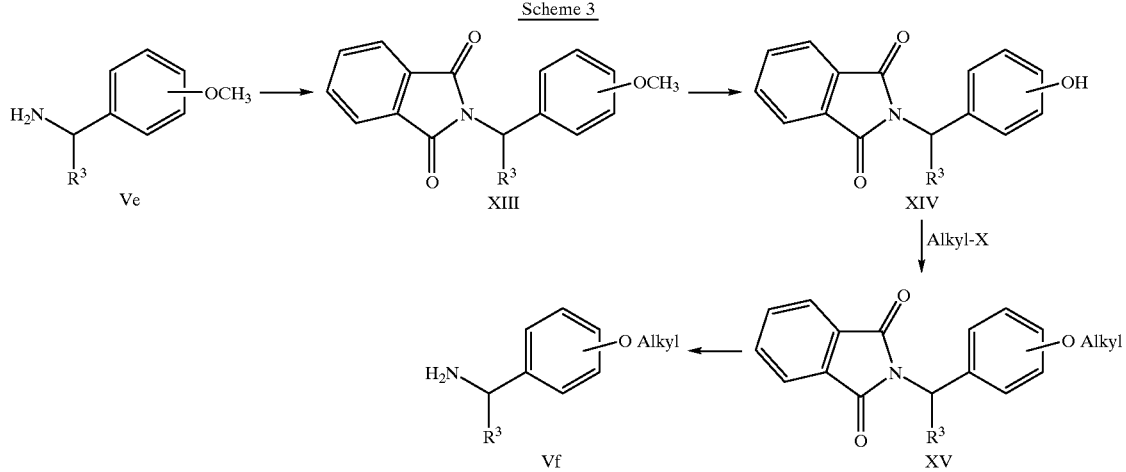

wherein R³ is as described above and X is a leaving group, such as, halogen, oxygen, or nitrogen.

Intermediates of formula Vf are prepared as set forth in Scheme 3. A primary amine of formula Ve, a known compound or compound prepared by known method, is protected with a group such as phthalimide to form the corresponding compound of formula XIII. The methyl ether of the compound of formula XIII is removed with a Lewis acid, preferably BBr₃ in a non polar solvent, such as methylene chloride, to form the corresponding phenol of formula XIV. The phenol of formula XIV is alkylated with an alkylating agent, such as, alkyl halide, an alkyl tosylate, or an alkyl mesylate in the presence of a base, preferably NaH to form the corresponding compound of formula XV. The compound of formula XV can be deprotected, for example, with hydrazine in refluxing alcohol, preferably ethanol, to form the corresponding primary amine of formula Vf.

Scheme 4

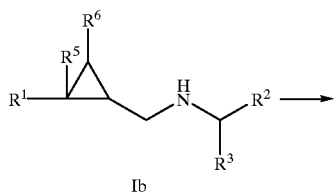

-continued

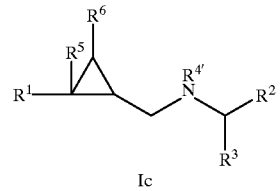

wherein the substituents are as described above except that when R² is phenyl substituted with hydroxyl or hydroxyalkyl, the hydroxyl group is first protected with a protecting group such as t butyldimethylsilyl group.

Compounds of formula I wherein R⁴ is other than H (Ic) can be synthesized as shown in Scheme 4 by treating the compound of formula Ib with an appropriate acylating or alkylating agent in the presence of a non-nucleophilic base, such as triethylamine or Hunig's base.

Scheme 5

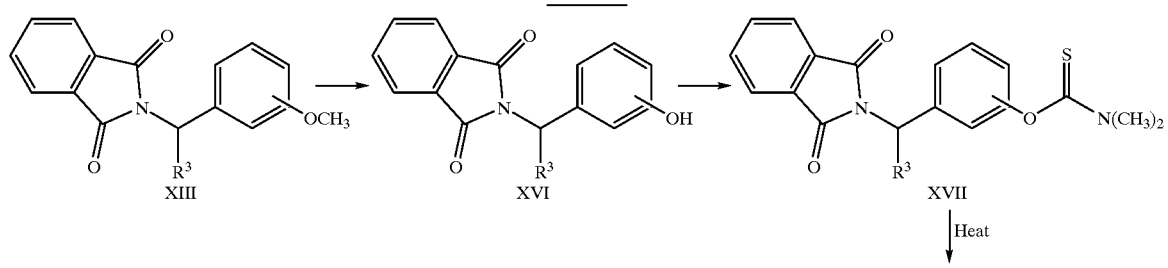

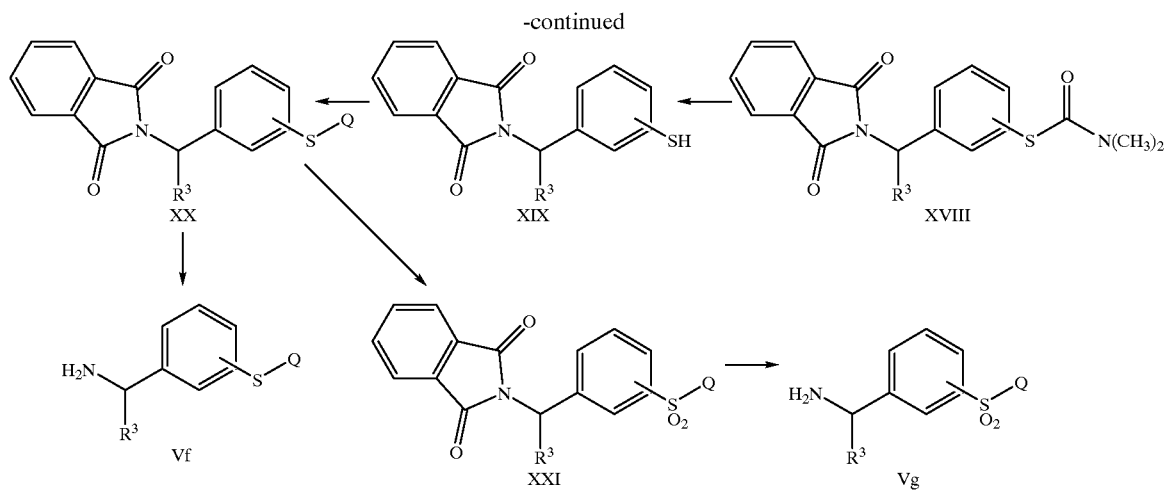

wherein $R^3$ is as described above and Q is alkyl or aryl.

Starting materials of formula Vf and Vg can be obtained as shown above in Scheme 5. A compound of formula XIII, can be demethylated with $BBr_3$ to form the corresponding compound of formula XVI. A compound of the formula XVI can be acylated with an agent such as dimethylcarbamic chloride to yield a corresponding compound of formula XVII. The compound of formula XVII can be heated, for example in refluxing diphenyl ether, to form the corresponding thiocarbamate of formula XVIII (*Synthesis* 1992, 112). The compound of formula XVIII can be hydrolyzed or saponified with aqueous acid or aqueous base, such as hydrochloric acid or sodium hydroxide, to form the corresponding compound of formula XIX. The compound of formula XIX can be alkylated for example, with an alkyl halide or arylated (*J. Org. Chem* 1995, 60,7144) to the corresponding compound of formula XX. The compound of formula XX can be deprotected with a reagent such as hydrazine to yield the corresponding compound of formula Vf which can be converted to the cyclopropane product of formula I by one of the methods above. Alternatively, the compound of formula XX can be oxidized to the corresponding sulfone of formula XXI with an oxidizing agent such as metachloroperoxybenzoic acid (mCPBA) (*Helv. Chim. Acta* 1984, 67, 1316). The compound of formula XXI can be deprotected with a reagent such as hydrazine to yield the corresponding compound of formula Vg, which can be converted to the cyclopropane of formula I by the method in Scheme 1b.

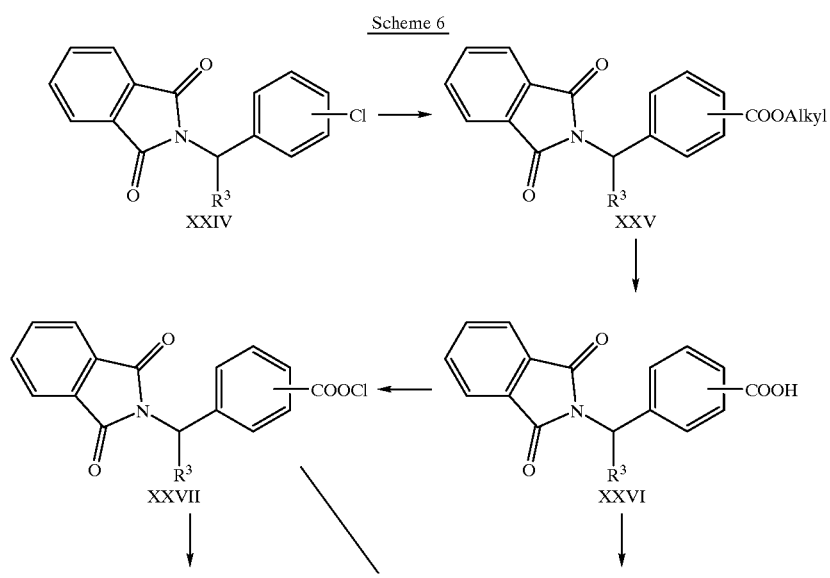

Scheme 6

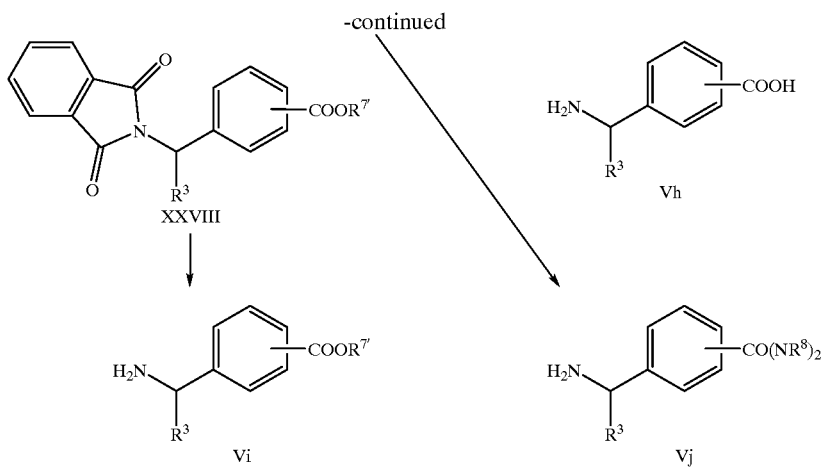

wherein $R^3$ and $R^8$ are as described above and $R^{7'}$ is alkyl.

As set forth in Scheme 6 above, a compound of formula XXIV, a known compound or compound prepared by known methods, can be converted to the corresponding ester of formula XXV (*Chem. Comm.* 1990, 426). The compound of formula XXV can be converted to the compound of formula XXVI by a method such as acid hydrolysis with a reagent such as aqueous HCl, at elevated temperature, near reflux. A compound of formula XXVI can be converted to a corresponding compound of formula Vh by deprotection with a reagent such as hydrazine in a polar solvent such as ethanol at temperatures near refluxing ethanol. Alternatively, a compound of formula XXVI can be converted to a corresponding acid chloride of formula XXVII by reaction with a reagent such as thionyl chloride in an inert solvent such as methylene chloride, at or below room temperature. The compound of formula XXVII can be converted to a corresponding ester of formula XXVIII with an alcohol, such as 2-(dimethylamino)ethanol, reaction at or below room temperature. The compound of formula XXVIII can be deprotected to a compound of formula Vi by a known method such as reacting with ammonia in a polar solvent, such as ethanol, at temperatures near refluxing ethanol. Alternatively, a compound of formula XXVII can be aminated and deprotected to a compound of formula Vj by a known method such as by reacting with dimethylamine in an inert solvent such as methylene chloride, at or below room temperature.

CALCIUM-SENSING RECEPTOR ACTIVITY IN VITRO AND IN VIVO

In vitro potency is measured via calcium mobilization in a fluorescence assay using HEK 293 cells transfected to express the same calcium sensing receptor as found in the human parathyroid gland. In this assay calcium-sensing receptor agonists and antagonists are detected. The assay is conducted in a 96-well plate format with the use of FLIPR (fluorescent imaging plate reader; Molecular Devices, Sunnyvale, Calif.). The HEK 293 cell media is replaced with the fluorescence dye FLUO-3AM and Pluronic detergent in FLIPR assay buffer. Cells are incubated 60 min (in the dark, at room temperature), then washed with assay buffer and placed in FLIPR. Images are collected by FLIPR in the absence of test compound, then in the presence of test compound (at 25 M) and then after addition of a calcium challenge (at 1 mM). In the agonist assay the difference between maximum and minimum fluorescence values is measured following test compound addition. Hits have a change in fluorescence greater than or equal to 50% of that seen with a 1 mM calcium standard. In the antagonist assay the difference between maximum and minimum fluorescence values is measured following the calcium challenge addition. When compared to challenge in the absence of test compound, hits reduce fluorescence by at least 50%. In vivo activity is measured via parathyroid hormone (PTH) supression by test compounds in a rat model. Compound is administered orally using 0.5% Tween 80 in distilled water as vehicle, with a volume of approximately 10 mL/kg body weight. Blood samples are taken at 15 minutes (and 4 h if required) post oral dosing. Serum PTH levels are determined with an immunoradiometric assay.

TABLES

Not all compounds were tested in each of the screens. A hyphen filling the space for a particular compound indicates that the compound was not tested in that screen. Table 1 lists those compounds where stereochemistry is not controlled. Each entry represents a mixture of cis and trans cyclopropanes (R,S; S,R; R,R; S,S) with R absolute configuration when $R^3=CH_3$. Table 2 lists compounds that are trans at the cyclopropane (R,R; S,S) with R absolute configuration at the benzylamine position, or without stereochemistry at the benzylamine. Table 3 lists compounds with R,R absolute stereochemistry at the cyclopropane and a mixture of stereochemistry at the benzylamine position. Table 4 lists compounds with R,R,R absolute configuration. Table 5 lists compounds substituted at the amine. Table 6 lists IA and all other stereoisomers. Table 7 lists those compounds not included in any of the previous six tables. Table 8 lists stereoisomers of compound no. 20. In vitro data in Table 1 is percent activation of the calcium-sensing receptor versus baseline. In vitro data in Tables 2–7 is expressed as a CS50, where potency is at 50% of the calcium standard potency, and the unit is $\mu M$. In vivo data represents % blood serum PTH vs. vehicle at 30 mg/kg test compound, levels measured after 15 minutes.

TABLE 1

| # | X¹ | y¹ | In Vitro | In Vivo | MS (MH+) |
|---|---|---|---|---|---|
| 1 | 2,5-diMe | 3-CH$_3$O | 13 | +31.4 | 310 |
| 2 | 3,4-(CH)$_4$ | 3-CH$_3$O | 13 | — | 332 |
| 3 | H | 3-CH$_3$O | 39 | −62.1 | 282 |
| 4 | 2-Cl | 3-CH$_3$O | 33 | −11.9 | 316 |
| 5 | 3-Cl | 3-CH$_3$O | 32 | — | 316 |
| 6 | 4-Cl | 3-CH$_3$O | 9 | −9.3 | 316 |
| 7 | 2-Br | 3-CH$_3$O | 11 | — | 360/362 |
| 8 | 2-CF$_3$ | 3-CH$_3$O | 26 | — | 350 |

TABLE 2

R$_3$ = H or CH$_3$
trans substitutions on cyclopropane

| # | R¹ | R² | R3 | In Vitro | In Vivo | MS (MH+) |
|---|---|---|---|---|---|---|
| 9 | 2-PYRIDYL | 3-CH$_3$OPh | CH$_3$ | 6.5 | — | 282 (M +) |
| 10 | 3-PYRIDYL | 3-CH$_3$OPh | CH$_3$ | 37.1 | — | 284 |
| 11 | 4-PYRIDYL | 3-CH$_3$OPh | CH$_3$ | >25 | — | 282 (M +) |
| 12 | 2-CH$_3$Ph | 3-CH$_3$OPh | CH$_3$ | 8.8 | −95.8 | 296 |
| 13 | 3-CH$_3$Ph | 3-CH$_3$OPh | CH$_3$ | 9.5 | −98.2 | 296 |
| 14 | 2-CF$_3$Ph | 3-CH$_3$OPh | CH$_3$ | 52.2 | −34.7 | 350 |
| 15 | 3-CF$_3$Ph | 3-CH$_3$OPh | CH$_3$ | 13.5 | +4.2 | 350 |
| 16 | 4-CF$_3$Ph | 3-CH$_3$OPh | CH$_3$ | >25 | −14.4 | 350 |
| 17 | 2-FPh | 3-CH$_3$OPh | CH$_3$ | 5.0 | −94.8 | 300 |
| 18 | 2-FPh, ONE DIASTER | 3-CH$_3$OPh | CH$_3$ | 11.3 | −83.9 | 299 (M+) |
| 19 | 2-FPh, ONE DIASTER | 3-CH$_3$OPh | CH$_3$ | 9.6 | −89.2 | 299 (M+) |
| 20 | 3-FPh | 3-CH$_3$OPh | CH$_3$ | 11.0 | −95.2 | 300 |
| 21 | 3-FPh, ONE DIASTER | 3-CH$_3$OPh | CH$_3$ | 10.9 | −78.7 | 299 (M+) |
| 22 | 3-FPh, ONE DIASTER | 3-CH$_3$OPh | CH$_3$ | 9.3 | −93.4 | 299 (M+) |
| 23 | 4-FPh | 3-CH$_3$OPh | CH$_3$ | 13.5 | −55.0 | 300 |
| 24 | 2,6-diFPh | 3-CH$_3$OPh | CH$_3$ | 11.9 | −85.4 | 318 |
| 25 | 2-THIENYL | 3-CH$_3$OPh | CH$_3$ | 7.1 | −89.0 | 288 |
| 26 | 3-THIENYL | 3-CH$_3$OPh | CH$_3$ | 3.4 | — | 288 |
| 27 | 2-(N-METHYL-PYRROLO) | 3-CH$_3$OPh | CH$_3$ | 7.8 | — | 285 |
| 28 | Ph | 2-PYRIDYL | H | >25 | +72.0 | 239 |
| 29 | Ph | 3-PYRIDYL | H | >25 | +87.8 | 239 |
| 30 | Ph | 4-PYRIDYL | H | >25 | +70.1 | 239 |
| 31 | Ph | 3-CH$_3$OPh | H | >25 | −26.5 | 268 |
| 32 | 2,5-diMeph | 3-CH$_3$OPh | CH$_3$ | 12.4 | −13.5 | 310 |
| 33 | 2,5-diMePh | 3-CH$_3$OPh | CH$_3$ | >25 | −47.6 | 310 |
| 34 | 2,4-(NO$_2$)2Ph | 3-CH$_3$OPh | CH$_3$ | >25 | — | 372 |
| 35 | 2-(5-Cl-Thienyl) | 3-CH$_3$OPh | CH$_3$ | | −15.4 | 322 |
| 36 | 2-(5-CH$_3$-Thienyl) | 3-CH$_3$OPh | CH$_3$ | | −34.2 | 302 |
| 37 | 2-(4-Br-Thienyl) | 3-CH$_3$OPh | CH$_3$ | | −24.8 | 366/368 |
| 38 | 2-(3-CH$_3$-Thienyl) | 3-CH$_3$OPh | CH$_3$ | | −51.0 | 302 |

TABLE 3

| # | Y | R3 | In Vitro | In Vivo | MS (MH+) |
|---|---|---|---|---|---|
| 39 | CF$_3$O | CH$_3$ | — | 0.0 | 336 |
| 40 | CH$_3$ | CH$_3$ | >25 | −51.2 | 266 |
| 41 | CF$_3$ | CH$_3$ | >25 | −21.4 | 320 |
| 42 | CH$_2$CH$_3$ | CH$_3$ | >25 | −78.9 | 280 |
| 43 | CH$_3$O | CH$_2$CH$_3$ | >25 | −6.3 | 296 |
| 44 | CH$_3$O | gem-(CH$_3$)$_2$ | >25 | −25.8 | 296 |
| 45 | F | CH$_3$ | >25 | −19.6 | 270 |
| 46 | Cl | CH$_3$ | >25 | −15.9 | 286 |
| 47 | 3,4-(—OCH$_2$O—) | CH$_3$ | >25 | −67.3 | 296 |

TABLE 4

| # | W | In Vitro | In Vivo | MS (MH+) |
|---|---|---|---|---|
| 48 | H | 8.7 | −41.7 | 268 |
| 49 | CH$_3$ | 5.0 | −83.6 | 282 |
| 50 | CH$_2$CH$_3$ | 11.9 | −57.0 | 296 |
| 51 | CH(CH$_3$)$_2$ | >25 | −7.3 | 310 |
| 52 | c-PENTYL | 12.2 | 26.6 | 336 |

TABLE 5

| # | Z | In Vitro | In Vivo | MS (M+) |
|---|---|---|---|---|
| 53 | CH$_3$ | >25 | −6.4 | 323 |
| 54 | CH$_2$CH$_3$ | >25 | −33.7 | 337 |
| 55 | C(CH$_3$)$_3$ | >25 | — | 365 |
| 56 | CH$_3$O | >25 | −40.9 | 339 |
| 57 | OCH$_2$CH(CH$_3$)$_2$ | >25 | −5.3 | 381 |
| 58 | CH$_2$NH(t-BOC) | >25 | −12.7 | 439 (MH+) |

TABLE 6

Absolute Stereochemistry at 1, 2, and 3

| # | 1 | 2 | 3 | In Vitro | In Vivo | MS (MH+) |
|---|---|---|---|----------|---------|----------|
| 59 | R | R | R | 5.0 | −83.6 | 282 |
| 60 | S | S | R | 12.9 | −42.1 | 282 |
| 61 | S | R | R | 11.2 | 0.0 | 282 |
| 62 | R | S | R | 17.6 | 0.0 | 282 |
| 63 | R | R | S | >25 | −40.1 | 282 |
| 64 | S | S | S | >25 | −11.7 | 282 |
| 65 | R | S | S | >25 | −38.8 | 282 |
| 66 | S | R | S | >25 | −61.8 | 282 |

TABLE 8

Absolute Stereochemistry at 1, 2, and 3.

| # | 1 | 2 | 3 | In Vitro | In Vivo | MS (MH+) |
|---|---|---|---|----------|---------|----------|
| 71 | S | S | R | — | −78.7 | 300 |
| 72 | R | R | R | — | −93.4 | 300 |
| 73 | — | — | R | — | −52.5 | 300 |
| 74 | — | — | R | — | −2.6 | 300 |
| 75 | S | S | S | — | −0.9 | 300 |
| 76 | R | R | S | — | +16.8 | 300 |
| 77 | — | — | S | — | +2.1 | 300 |
| 78 | — | — | S | — | +21.4 | 300 |

TABLE 7

| # | Structure | In Vitro | In Vivo (%) | MS (MH+) |
|---|-----------|----------|-------------|----------|
| 67 | 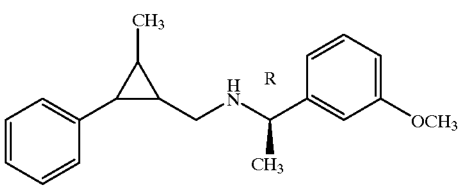 | 10.1 | −92.9 | 296 |
| 68 | 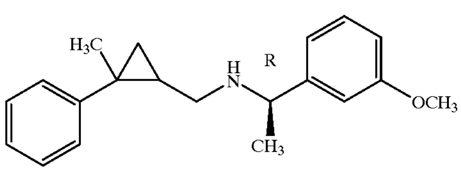 | >25 | −94.5 | 296 |
| 69 | 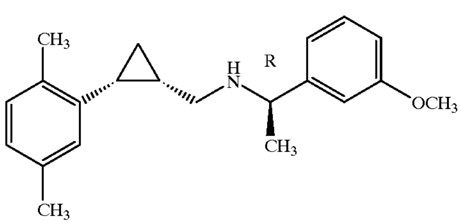 | >25 | −53.9 | 310 |
| 70 | 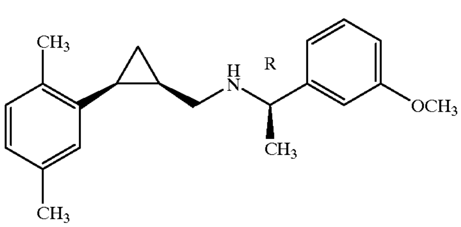 | 21.0 | −24.7 | 310 |

To prepare the pharmaceutical compositions of this invention, one or more compounds or salts thereof, as the active ingredient, is intimately admixed with a pharmaceutical carrier according to conventional pharmaceutical compounding techniques, which carrier may take a wide variety of forms depending on the form of preparation desired for administration, for example, oral or parenteral. In preparing the compositions in oral dosage form, any of the usual pharmaceutical media may be employed. Thus, for liquid oral preparations, such as, for example, suspensions, elixirs and solutions, suitable carriers and additives include water, glycols, oils, alcohols, flavoring agents, preservatives, coloring agents and the like; for solid oral preparations such as, for example, powders, capsules and tablets, suitable carriers and additives include starches, sugars, diluents, granulating agents, lubricants, binders, disintegrating agents and the like. Because of their ease in administration, tablets and capsules represent the most advantageous oral dosage form, in which case solid pharmaceutical carriers are obviously employed. If desired, tablets may be sugar coated or enteric coated by standard techniques. For parenterals, the carrier will usually comprise sterile water, though other ingredients, for example, for purposes such as aiding solubility or for preservation, may be included. Injectable suspensions may also be prepared, in which case appropriate liquid carriers, suspending agents and the like may be employed. The pharmaceutical compositions herein will preferably contain per dosage unit, e.g., tablet capsule, powder, injection, teaspoonful and the like, from about 10 to 1000 mg of the active ingredient, although other unit dosages may be employed.

In therapeutic use for treating disorders related to calcium imbalance and metabolism in mammals, the compounds of this invention may be administered in an amount of from about 0.3 to 30 mg/kg 3 times per day orally, particularly preferred is 1 to 10 mg/kg preferably three times a day. In addition, the compounds may be administered via injection at 0.1 to 10 mg/kg per day. Determination of optimum dosages for a particular situation is within the capabilities of formulators.

In order to illustrate the invention, the following examples are included. These examples do not limit the invention. They are meant to illustrate and suggest a method of practicing the invention. Although there are other methods of practicing this invention, those methods are deemed to be within the scope of this invention.

EXAMPLE 1

N-((R,R)-2-phenylcyclopropanylmethyl)-1-(R)-(3-methoxyphenyl)ethylamine (a) (N)-Hydroxysuccinimide-(O)-diazoacetate (3.5 g, 19.1 mmol) in 75 mL $CH_2Cl_2$ was added dropwise to a solution of (R)-(3-methoxyphenyl)ethylamine (3.0 g, 20.1 mmol) and triethylamine (4.0 mL, 28.7 mmol) in 125 mL $CH_2Cl_2$, at 0° C. under an $N_2$ atmosphere. This was stirred for 0.5 h, then ice bath was removed and stirred for 1.5 h at room temperature. Solvent was removed, clean on silica. 3.4 g of (R)-(3-methoxyphenyl)ethyl diazoacetamide (15.7 mmol, 82%) was obtained. NMR ($^1$H, CDCl$_3$) 7.30 (t, 1H, J=8.5), 6.85 (m, 3H), 5.1 (br m, 1H), 3.79 (s, 3H), 1.48 (d, 3H, J=8.5). (b) The diazoacetamide (312 mg, 1.4 mmol) in 10 mL dichloroethane was added dropwise to styrene (1.4 mL, 12 mmol) and rhodium acetate dimer (5 mg, 0.011 mmol, 1 mol %) at room temperature, open to air. This was shaken at room temperature overnight, then heated to 70° C. for 2 h. Solvent was removed and clean on silica. 181 mg (0.61 mmol, 44%) of the cyclopropyl amide was obtained as a mixture of four diastereomers (14.7:8.8:1.4:1). MS (GC/MS) m/z 295 (M$^+$). (c) The cyclopropane (164 mg, 0.56 mmol) was dissolved in 16 mL THF, cooled to 0° C. and borane-THF (1.0 M solution, 2.24 mmol) was added via syringe. This was refluxed overnight, then cooled to 0° C. and 2 mL of 6 N HCl was added. This was stirred for 2 h, THF was removed, then 9 mL saturated aqueous $Na_2CO_3$ was added. This was extracted with 2×7 mL $CH_2Cl_2$ and 5 mL ethyl acetate. Organics were combined, diluted with 12 mL ether, and washed with brine. Organics were dried ($Na_2SO_4$), filtered, and solvent was removed. 156 mg (0.56 mmol, 99%) of N-((R,R)-2-phenylcyclopropanylmethyl)-1-(R)-(3-methoxyphenyl) ethylamine was obtained MS (CI) m/z 282 (MH$^+$).

Compounds 1, 2, 3, 4, 5, 6, 7 and 8 of Table 1 were prepared in a manner analogous to Example 1.

EXAMPLE 2

N-((R,R)-2-phenylcyclopropanylmethyl)-1-(R)-(3-methoxyphenyl)ethylamine (a) trans-2-Phenylcyclopropanecarboxylic acid (4.7 g, 29 mmol) was resolved to the (R,R) enantiomer with dehydroabietylamine (8.5 g, 29.8 mmol) as reported in *J. Med. Chem.* 1972, 15, 1187. The amine salt (3.5 g, 7.8 mmol, 54% of the R,R acid) was obtained. m.p. 168.5–170.0° C. (lit 174.0–174.5° C.); [ ]$^{25}_D$–75.6 (lit –80.2). (b) The (R,R)-2-phenylcyclopropanecarboxylic acid (7.5 g, 46 mmol) and (R)-3-methoxyphenyl)ethylamine (9.5 g, 63 mmol) were converted to the amide by the method reported in *Aust. J. Chem.* 1984, 37, 1709. Recrystallization from acetone/hexane yielded 7.55 g (25.5 mmol, 56%) of the amide [1R-[1a(R*),2b]]-2-phenyl-N-(1-(3-methoxyphenyl)ethyl) cyclopropanecarboxamide. m.p. 149.5–150.0° C. A second crop yielded 1.59 g (5.4 mmol, 12%) of the amide. m.p. 148.0–149.5° C. (c) [1R-[1a(R*),2b]]-2-phenyl-N-(1-(3-methoxyphenyl)ethyl)cyclopropanecarboxamide (13.6 g, 46 mmol) was dissolved in 320 mL THF and cooled to 0° C., under $N_2$. $BH_3$·THF (164 mL, 164 mmol) was added dropwise. Upon complete addition, the solution was heated to reflux, overnight. The solution was cooled to 0° C. and 165 mL of 6 N HCl was carefully added. This was stirred open to air for two hours. THF was removed in vacuo. The aqueous residue was basified to pH 9 with $Na_2CO_3$ solution and extracted with 5×100 mL $CH_2Cl_2$. The combined extracts were washed with 100 mL water and 100 mL of 1:1 water/brine. The organics were dried ($Na_2SO_4$), filtered, and solvent was removed. Obtain 13 g (46 mmol, 99%) of N-((R,R)-2-phenylcyclopropanylmethyl)-1-(R)-(3-methoxyphenyl)ethylamine was obtained. NMR (1H, CDCl3) 7.3–6.73 (m, 9H), 3.8 (m, 4H), 2.50 (d, 2H, J=8), 1.64 (m, 1H), 1.22 (d, 3H, J=8) 1.0–0.75 (m, 3H). MS (CI) m/z 282 (MH$^+$).

EXAMPLE 3

N-(trans-2-(3-fluorophenyl)cyclopropanylmethyl)-1-(R)-(3-methoxyphenyl)ethylamine (a) 3-Fluorostyrene (9.7 mL, 82 mmol) and ethyl diazoacetate (8.6 mL, 82 mmol) were reacted by the method reported in *Org. Syn. Coll. Vol. VI*, 1988, 913. The product was purified on silica. 9.4 g of ethyl 2-(3-fluorophenyl) cyclopropane carboxylate (45 mmol, 55%) was obtained. MS (GC/MS, EI) 208 (M$^+$). (b) The trans ester was selectively hydrolyzed from the cis/trans mixture by the method reported in *Org. Syn. Coll. Vol. VI*, 1988, 913. Recrystallize from hexane to yield 2.5 g (13.9 mmol, 89% of the trans) of trans-2-(3-fluorophenyl)cyclopropane carboxylic acid. (c)

The trans-2-(3-fluorophenyl)cyclopropane carboxylic acid (400 mg, 2.2 mmol) and (R)-3-methoxyphenyl ethylamine (280 mg, 1.9 mmol) were converted to the diastereomeric amides by the method reported in *Aust. J. Chem.* 1984, 37, 1709. 446 mg (1.4 mmol, 75%) of trans-2-(3-fluorophenyl)-N-(1(R))-(3-methoxyphenyl)ethyl)cyclopropane carboxamide was obtained. MS (GC/MS, EI) 313 (M$^+$). (d) The mixture of diastereomeric amides (550 mg, 1.8 mmol) were reduced to the amines with BH$_3$.THF (7 mL, 7.0 mmol) in 10 mL THF. Upon complete addition, the solution was heated to reflux, overnight. The solution was cooled to 0° C. and 7 mL of 6 N HCl was carefully added. This was stirred open to air for two hours, THF was removed in vacuo. The aqueous residue was basified to pH 9 with Na$_2$CO$_3$ solution and extracted with 3×20 mL CH$_2$Cl$_2$. The combined extracts were washed with 20 mL water and 20 mL of 1:1 water/brine. The organics were dried (Na$_2$SO$_4$), filtered, and solvent was removed. 520 mg of N-(trans-2-(3-fluorophenyl)cyclopropanylmethyl)-1-(R)-(3-methoxyphenyl)ethylamine (1.8 mmol, 99%) was obtained as an oil. MS (CI) m/z 300 (MH$^+$).

Compounds 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 59, 60, 61, 62, 63, 64, 65, 66, 67, 68, 69 and 70 of Tables 2, 6 and 7 were prepared in a manner analogous to Example 3.

EXAMPLE 4

N-((R,R)-2-phenylcyclopropanylmethyl)-1-(3-methoxyphenyl)propylamine (a) 3-Ethylacetophenone (10 g, 68 mmol) was added to hydroxylamine hydrochloride (9.5 g, 135 mmol) and pyridine (27.4 mL, 340 mmol) in 100 mL ethanol and the mixture was heated to 65° C. overnight, under N$_2$. Solvent was removed, the residue was taken up in 60 mL ether and 20 mL dichloromethane and washed with 2×25 mL water, 4×25 mL 10% aq. copper sulfate, 2×25 mL water, and 2×25 mL brine. The organics were dried (Na$_2$SO$_4$), filtered, and solvent was removed. 10.4 g (75 mmol, 99%) of 3-ethylacetophenone oxime was obtained as an oil. NMR (1H, CDCl3) 7.5–7.2 (m, 4H), 2.68 (q, 2H, J=7.7), 2.33, (s, 3H), 1.27 (t, 3H, J=7.7). (b) The oxime was reduced to the primary amine by the method reported in *Tet. Lett.* 1990, 31, 4011. The hydrochloride salt was converted to the free amine by exposure to aqueous K$_2$CO$_3$ and isolation of the organic with 1:1 ether/ethyl acetate. 8.9 g (60 mmol, 80%) of 1-(3-ethylphenyl)ethylamine was obtained as an oil. MS (CI) m/z 150 (MH$^+$). The amine was converted to the amide with (R,R)-trans-2-phenylcyclopropanecarboxylic acid, then reduced to the amine as described in Example 2.

Compounds 39, 40, 41, 42, 43, 44 and 45 of Table 3 were prepared in a manner analogous to Example 4.

EXAMPLE 5

N-((R,R)-2-phenylcyclopropanylmethyl)-1-(R)-(3-ethoxyphenyl)ethylamine (a) (R)-3-methoxyphenyl)ethylamine (10 g, 66 mmol) was converted to the phthalimide by the method reported in *J. Heterocyclic Chem.* 1991, 28, 609. Obtained 15.1 g (53 mmol, 81%) of (R)-(3-methoxyphenyl)ethyl phthalimide as a white solid. GCMS (EI) m/z 281 (M$^+$). (b) The methyl ether of the imide (5 g, 18 mmol) was dissolved in 100 mL CH2Cl2, cooled to 0° C., and BBr$_3$ (1.0 M in CH$_2$Cl$_2$, 53 mL, 53 mmol) was added dropwise. The reaction was warmed to room temperature overnight. The reaction was cooled to 0° C. and 70 mL water was cautiously added, followed by 70 mL 1 N NaOH. This was washed with 3×100 mL ethyl acetate, the organics were combined and washed with NaHCO$_3$, water, and brine. The organics were dried (Na$_2$SO$_4$), filtered, and the solvent was evaporated to yield the phenol. 4.5 g (17 mmol, 95%) of the (R)-(3-hydroxyphenyl)ethyl phthalimide was obtained as a white solid. GC/MS (EI) m/z 267 (M$^+$). NMR (CDCl3) 7.78 (m, 2H), 7.66 (m, 2H), 7.20 (t, 1H, J=8.0), 7.08 (m, 2H), 6.79 (m, 1H), 5.53 (q, 1H, J=7.5), 1.91 (d, 3H, J=7.5). (c) The phenol (500 mg, 1.9 mmol) was dissolved in 100 mL acetone, K$_2$CO$_3$ (517 mg, 3.7 mmol) was added, followed by iodoethane (0.2 mL, 2.2 mmol) and the mixture was stirred at 60° C. for 24 h. Water was added and the mixture was washed with 3×100 mL ether. The combined organics were washed with 1 N NaOH and water, then dried (Na$_2$SO$_4$). The solution was filtered and solvent removed. 350 mg (1.2 mmol, 63%) of (R)-(3-ethoxyphenyl)ethyl phthalimide was obtained as an oil. GCMS (EI) m/z 295 (M$^+$). (d) The imide (350 mg, 1.2 mmol) was dissolved in 40 mL ethanol, hydrazine (0.3 mL, 9.7 mmol) was added and the mixture was heated to reflux for 3 h. Stirring continued overnight at room temperature. The solid was filtered, then solvent was evaporated to yield the product. 178 mg (1.1 mmol, 90%) of (R)-3-(ethoxyphenyl)ethylamine was obtained as a pale yellow oil. MS (CI) m/z 166 (MH$^+$). The amine was converted to the amide with (R,R)-2-phenylcyclopropanecarboxylic acid, then reduced to the amine using the method in Example 2.

Compounds 48, 49, 50, 51 and 52 were prepared in a manner analogous to Example 5.

EXAMPLE 6

N-((R,R)-2-phenylcyclopropanylmethyl)-N-methylcarbamoyl-1-(R)-(3-methoxyphenyl)ethylamine N-((R,R)-2-phenylcyclopropanylmethyl)-1-(R)-(3-methoxyphenyl)ethylamine (150 mg, 0.53 mmol) was dissolved in 7 mL CH$_2$Cl$_2$. DMAP (65 mg, 0.53 mmol) and methyl chloroformate (0.05 mL, 0.64 mmol) were added and the the mixture was stirred overnight at room temperature. The organic mixture was diluted with 10 mL solvent, washed with 3×10 mL 10% aq. HCl and 10 mL water. The organics were dried (Na$_2$SO$_4$), filtered, and solvent was removed in vacuo. Clean on silica. Obtain 119 mg (0.35 mmol, 66%) of N-((R,R)-2-phenylcyclopropanylmethyl)-N-methylcarbamoyl-1-(R)-(3-methoxyphenyl)ethylamine as an oil. GC/MS (EI) m/z 339 (M$^+$).

Compounds 53, 54, 55, 56, 57 and 58 of Table 5 were prepared in a manner analogous to Example 6.

EXAMPLE 7

N-((R,R)-2-phenylcyclopropanylmethyl)-1-(3-chlorophenyl)ethylamine

3-Chloroacetophenone was reduced to the primary amine using the method described in *J. Med. Chem.* 1990, 33, 1910. The amine, without further purification, was converted to the amide with (R,R)-2-phenylcyclopropanecarboxylic acid and reduced to the amine using the method in Example 2. MS (CI) m/z 286.

Compounds 46 and 47 of Table 3 were prepared in a manner analogous to Example 7.

EXAMPLE 8

N-((RR)-2-phenylcyclopropylmethyl)-2-(3-methoxyphenyl) propylamine

Ethyl 3-methoxybenzoate (10 g, 56 mmol) was dissolved in 55 mL ether, cooled to −78° C., and treated with 55 mL 3.0 M methylmagnesium bromide in ether. The reaction was warmed to room temperature, stirred overnight, and excess reagent was quenched by addition of water and 6 M $H_2SO_4$ to the reaction at 0° C. 8.2 g (49 mmol, 89%) of 2-(3-methoxyphenyl)propan-2-ol was obtained as a colorless oil. NMR (1H, CDCl3): 7.25 (m, 1H), 7.07 (m, 2H), 6.79 (m, 1H), 3.80 (s, 3H), 1.56 (s, 6H). The alcohol (8.2 g, 49 mmol) was converted to the azide by the method reported in *J. Org. Chem.* 1993, 58, 5886. 1.8 g (9.4 mmol, 19%) of 2-(3-methoxyphenyl)propylazide was obtained. NMR (1H, CDCl3) 7.5–6.7 (m, 4H), 3.8 (s, 3H), 1.55 (s, 6H). The azide (1.8 g, 9.4 mmol) was reduced to the amine with catalytic 10% Pd/C, H2 (40 psi), and 5 mL conc. HCl in 75 mL ethanol. 1.5 g (9.3 mmol, 99%) of 2-(3-methoxyphenyl)propyl-2-amine was obtained as an oil. MS (Cl) m/z 166 (MH+). The amine was converted to the amide with (R,R)-2-phenylcyclopropanecarboxylic acid, then reduced to the amine using the method in example 2.

EXAMPLE 9

N-((R,R)-2-phenylcyclopropanylmethyl)-1-(R)-(3-methoxyphenyl)ethylamine as the hydrochloride salt Lithium borohydride (14.7 g, 677.0 mmol was dissolved in 400 mL of THF and treated with [1R-[1a(R*),2b]]-2-phenyl-N-(1-(3- methoxyphenyl)ethyl) cyclopropanecarboxamide (100.0 g, 338.5 mmol). The reaction mixture was heated to 60° C. and chlorotrimethylsilane (73.5 g, 677.0 mmol) was added dropwise. Upon complete addition, the solution was heated to reflux, for 4 h. The solution was cooled to ambient temperature and added to 600 mL of 6 N HCl at 15–20° C. The aqueous residue was basified with 265 g of 50% NaOH and extracted with 1×600 mL, then 1×400 mL tert-butyl methyl ether (MTBE). The combined extracts were washed with 500 mL water and 500 mL of brine. The organics were dried (MgSO4) then cooled to 0° C. and treated with 18.5 g gaseous HCl. The white crystalline HCl salt was collected via filtration and washed with 200 mL of MTBE. The product was dried under vacuum to afford 93.6 g (86.9%) of N-((R,R)-2-phenylcyclopropanylmethyl)-1-(R)-(3-methoxyphenyl)ethylamine as the hydrochloride salt. mp: 136.2–137° C.

What is claimed is:

1. A compound of the formula

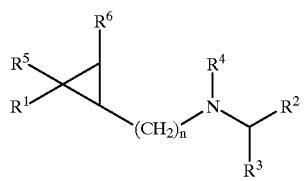

I wherein
$R^1$ is unsubstituted aryl; or aryl substituted with at least one substituent selected from the group consisting of $C_1$–$C_6$ alkyl, cycloalkyl, halogen, haloalkyl, nitro, and alkoxy;
$R^2$ is phenyl substituted with at least one substituent selected from $C_1$–$C_6$ alkyl, cycloalkyl, haloalkyl, chloro, fluoro, iodo, alkoxy, alkylthio, alkylsulfone, aryl sulfone, hydroxy, hydroxy alkyl, —$COOR^7$ and $CON(R^8)_2$; unsubstituted heteroaryl or heteroaryl substituted with at least one substituent selected from $C_1$–$C_6$ alkyl, cycloalkyl, haloalkyl, chloro, fluoro and iodo;

$R^3$ is hydrogen, $C_1$–$C_6$ alkyl or $C_1$–$C_6$ geminal dialkyl;
$R^4$ is hydrogen, $CON(R^9)_2$, $SO_2N(R^{10})_2$, $COR^{11}$ or $COOR^{12}$;
$R^5$, $R^6$, $R^7$, $R^8$, $R^9$, $R^{10}$, $R^{11}$ and $R^{12}$ are independently selected from hydrogen or alkyl; and
n is 1 or
pharmaceutically acceptable salts or stereochemically isomeric forms thereof.

2. The compound of claim 1, wherein $R^1$ is unsubstituted aryl or aryl substituted with halogen or $C_1$–$C_6$ alkyl; $R^2$ is unsubstituted pyridyl, pyridyl substituted with at least one of $C_1$–$C_6$ alkyl, cycloalkyl, haloalkyl, chloro, fluoro or iodo, or phenyl substituted with at least one substituent selected from $C_1$–$C_6$ alkyl, cycloalkyl, haloalkyl, chloro, fluoro, iodo, $C_1$–$C_6$ alkoxy, alkylthio, alkylsulfone, arylsulfone, hydroxy, hydroxyalkyl, —$COOR^7$ and $CON(R^8)_2$; $R^3$ is alkyl and $R^4$ is hydrogen, $CON(R^9)_2$, $COR^{11}$ or $COOR^{12}$.

3. The compound of claim 2, wherein $R^3$ is methyl and $R^4$ is hydrogen.

4. The compound of claim 2, wherein $R^1$ is unsubstituted phenyl or thiophene or phenyl or thiophene substituted with halogen or $C_1$–$C_6$ alkyl; $R^2$ is phenyl substituted with $C_1$–$C_6$ alkyl, chloro, fluoro, iodo or $C_1$–$C_6$ alkoxy.

5. The compound of claim 4, wherein $R^1$ is unsubstituted phenyl or thiophene and $R^2$ is phenyl substituted with $C_1$–$C_6$ alkyl, chloro, fluoro, iodo or $C_1$–$C_6$ alkoxy.

6. The compound of claim 5, wherein $R^3$ is methyl and $R^4$ is hydrogen.

7. The compound of claim 1, 2-N-((R,R)-2-phenylcyclopropanylmethyl)-1-(R)-(3-methoxyphenyl)ethylamine, represented by the formula

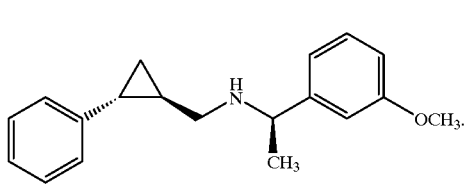

IA

8. A pharmaceutical composition comprising an effective amount of a compound as claimed in claim 1 and a pharmaceutically acceptable carrier.

9. A method of treating diseases related to calcium imbalance and metabolism comprising administering to a host in need thereof an effective amount of a compound of claim 1.

10. A method of claim 9, wherein the disease is hyperparathyroidism.

11. A method of claim 9, wherein the disease is osteoporosis.

12. A compound of the formula

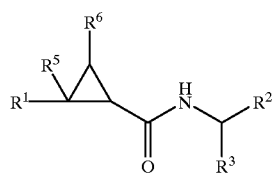

VIa wherein
$R^1$ is unsubstituted aryl; or aryl substituted with at least one substituent selected from the group consisting of $C_1$–$C_6$ alkyl, cycloalkyl, halogen, haloalkyl, nitro, and alkoxy;

R[2] is phenyl substituted with at least one substituent selected from $C_1$–$C_6$ alkyl, cycloalkyl, haloalkyl, chloro, fluoro, iodo, alkoxy, alkylthio, alkylsulfone, aryl sulfone, hydroxy, hydroxy alkyl, —COOR[7] and CON(R[8])$_2$; unsubstituted heteroaryl or heteroaryl substituted with at least one substituent selected from $C_1$–$C_6$ alkyl, cycloalkyl, haloalkyl, chloro, fluoro and iodo;

R[3] is hydrogen, $C_1$–$C_6$ alkyl or $C_1$–$C_6$ geminal dialkyl;

one of R[5] and R[6] is alkyl and the other is hydrogen or both R[5] and R[6] are alkyl; and R[7] and R[8] are independently selected from hydrogen or alkyl.

13. A process for preparing a compound of formula Ia

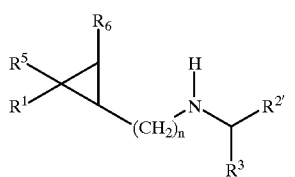

wherein

R[1] is unsubstituted aryl; or aryl substituted with at least one substituent selected from the group consisting of $C_1$–$C_6$ alkyl, cycloalkyl, halogen, haloalkyl, and alkoxy;

R[2'] is phenyl substituted with at least one substituent selected from $C_1$–$C_6$ alkyl, cycloalkyl, haloalkyl, chloro, fluoro, iodo, alkoxy, alkylthio, hydroxy, hydroxy alkyl, unsubstituted heteroaryl or heteroaryl substituted with at least one substituent selected from $C_1$–$C_6$ alkyl, cycloalkyl, haloalkyl, chloro, fluoro and iodo;

R[3] is hydrogen, $C_1$–$C_6$ alkyl or $C_1$–$C_6$ geminal dialkyl;

R[4] is hydrogen, CON(R[9])$_2$, SO$_2$N(R[10])$_2$, COR[11] or COOR[12];

R[5], R[6], R[9], R[10], R[11] and R[12] are independently selected from hydrogen or alkyl; and n is 1 or pharmaceutically acceptable salts or stereochemically isomeric forms thereof, comprising reacting a compound of formula VI

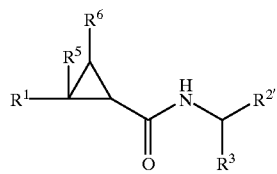

with lithium or sodium borohydride then adding chlorotrimethylsilane.

* * * * *